United States Patent [19]

Kirsh et al.

[11] Patent Number: 4,831,018
[45] Date of Patent: May 16, 1989

[54] POLYENE ANTIBIOTIC EMULSION FORMULATION

[75] Inventors: Richard L. Kirsh, Wayne; Louis J. Ravin, Plymouth Meeting, both of Pa.

[73] Assignee: SmithKline Beckman Corporation, Philadelphia, Pa.

[21] Appl. No.: 30,008

[22] Filed: Mar. 25, 1987

Related U.S. Application Data

[62] Division of Ser. No. 735,492, May 17, 1985, Pat. No. 4,707,470.

[51] Int. Cl.$^4$ .................... A61K 47/00; A61K 31/17; A61K 31/18; A61K 31/57
[52] U.S. Cl. ..................... 514/31; 514/938; 514/943; 536/6.5; 604/81
[58] Field of Search ............... 514/31, 938, 943; 604/81; 536/6.5

[56] References Cited

U.S. PATENT DOCUMENTS

| | | | |
|---|---|---|---|
| 4,158,707 | 6/1979 | Steffen et al. | 514/784 |
| 4,432,754 | 2/1984 | Urquhart et al. | 604/56 |
| 4,432,756 | 2/1984 | Urquhart et al. | 604/80 |
| 4,493,702 | 1/1985 | Urquhart et al. | 604/80 |
| 4,573,974 | 3/1986 | Ruschke | 604/81 |
| 4,707,470 | 11/1987 | Kirsh et al. | 514/31 |

Primary Examiner—Ronald W. Griffin
Attorney, Agent, or Firm—Mary E. McCarthy; Stuart R. Suter; Alan D. Lourie

[57] ABSTRACT

A polyene antibiotic emulsion formulation comprising a therapeutically effective amount of the antibiotic incorporated into an oil-in-water emulsion, and a method of treating an active infection in an animal caused by a microorganism with sterols in its cell membrane by parenterally administering the emulsion formulation to such animal.

4 Claims, No Drawings

POLYENE ANTIBIOTIC EMULSION FORMULATION

This is a division of pending application Ser. No. 735,492, filed May 17, 1985, now U.S. Pat. No. 4,707,470, issued Nov. 17, 1987.

BACKGROUND OF THE INVENTION

This invention relates to a novel polyene antibiotic emulsion formulation suitable for safe, parenteral administration of the polyene antibiotic, and a method for using such formulation.

The polyenes are macrolide antibiotics that selectively inhibit organisms whose membranes contain sterols. They are active against yeast, fungi, and other eukaryotic cells, but have no inhibitory action on the prokaryotic bacteria which lack sterols in their cell membranes. The antifungal activity of the polyenes is due to changes in the permeability of the membrane produced by antibiotic-sterol interaction. For example, treatment of fungal cells with amphotericin B, a polyene antibiotic, produces craters and vesiculation of the plasma membrane, but produces no holes or poles. It is thus believed that the altered permeability is the result of changes in the physical properties of the membranes resulting from avid binding of the polyenes to the membrane sterols which normally stabilize membrane function. The polyene-sterol interaction would then mediate a phase transition from an ordered state to a melted or random state, resulting in increased permeability.

The polyene antibiotic, amphotericin B, remains the cornerstone of antifungal therapy. It is active against most fungi that can cause deep-seated infections. However, even at recommended dosages, in its known parenteral formulations for administration, amphotericin B produces a number of side effects, of which nephrotoxicity is the most serious. Such side effects limit the quantity of amphotericin B which can be safely parenterally administered, and thus also limit the utility of such conventional formulations. Another polyene antifungal agent, nystatin, is also useful clinically. Because of its toxicity when administered parenterally in known formulations, its most important use is in the treatment of topical or superficial infections, especially those caused by Candida. All other known polyene antiobiotics are so toxic when administered parenterally that such a delivery route is not viable for administering therapeutic dosages of the antibiotic. Thus, it is clear that there is a real need for the safer, parenteral formulation of this invention which permits administration of conventional or larger dosages of polyene antibiotics, wherein said dosages are toxic in known formulations, without significantly reducing the pharmacologic efficacy of the antibiotic.

SUMMARY OF THE INVENTION

This invention relates to a polyene antibiotic emulsion formulation which comprises a therapeutically effective amount of a polyene antibiotic incorporated into an oil-in-water emulsion.

This invention also relates to a method of treating an active infection in an animal, wherein said infection is caused by a microorganism which has sterols in its cell membrane, which comprises parenterally administering to such animal a polyene antibiotic emulsion formulation containing a therapeutically effective amount of such antibiotic incorporated into an oil-in-water emulsion.

DETAILED DESCRIPTION OF THE INVENTION

The polyene antibiotics useful in the formulation and method of the subject invention include, but are not limited to, tetraenes such as nystatin, pentaenes such as aliomycin, methylpentatenes such as filipin, carbonylpentaenes such as mycoticin, hexaenes such as cryptocidine, carbonylhexaenes such as dermostatin, and heptaenes such as amphotericin B. Such antibiotics are commercially available or can be conventionally prepared by techniques known to one of skill in the art. Preferred polyene antibiotics include amphotericin B and nystatin. The most preferred polyene antibiotic is amphotericin B.

Any oil-in-water emulsion may be used in the formulation of the subject invention if it contains a non-toxic oil or fat that can be parenterally administered. Such oils or fats include, but are not limited to, soybean oil, sesame seed oil, peanut oil, corn oil, isopropyl myristate and glyceryl tripelargonate. Such oil-in-water emulsions are commercially available or can be conventionally prepared by techniques known to one of skill in the art. The amount of oil or fat in the oil-in-water emulsion can range from about 5 to about 40%. The preferred amount of oil or fat to water in the oil-in-water emulsion is from about 10 to about 20%. Intralipid ® 10% and Intralipid ® 20%, soybean oil-in-water emulsions, are the preferred oil-in-water emulsions, and are available commercially from Cutter Labs., Inc., Berkeley, Calif. Intralipid ® 20% is the most preferred oil-in-water emulsion.

In order to incorporate the desired polyene antibiotic into the desired oil-in-water emulsion to create the emulsion formulation of this invention, it is necessary to first solubilize the desired antibiotic in an appropriate solvent. By "appropriate solvent" is meant any non-toxic solvent which will enable the desired antibiotic to become incorporated into the desired oil-in-water emulsion as a microemulsion. Appropriate solvents include, but are not limited to, polar solvents such as dimethylacetamide (DMA), pyridine, dimethylformamide (DMF), dimethysulfoxide (DMSO), polyethyleneglycol (PEG) or diethylcarbonate. Choice of solvents depends on the solubility of the polyene antibiotic. DMA is the preferred solvent for solubilizing the desired polyene antibiotic, particularly for solubilizing amphotericin B or nystatin. In order to incorporate higher than conventional dosages of the polyene antibiotic into the oil-in-water emulsion, it may be necessary to use a co-solubilizing agent, such as deoxycholic acid sodium salt, polysorbate 80, polyethyleneglycol, Tween 80 or any other co-solubilizing agent which is miscible with the solubilizing agent chosen.

The formulation of this invention permits safe, parenteral administration of a conventional dosage of a polyene antibiotic to animals without significantly affecting the efficacy of the antibiotic. Furthermore, the formulation of this invention permits safe, parenteral administration of a higher than conventional dosage of a polyene antibiotic to animals, i.e., the formulation of the subject invention increases the therapeutic index of the polyene antibiotic it contains because it increases the maximum tolerated dose of the polyene antibiotic.

It will be appreciated by one of skill in the art that the actual preferred dosage of a polyene antibiotic used in the formulation of this invention will vary according to the particular polyene antibiotic being used, the mode of parenteral administration and the particular site employed, the particular host being treated, and the particular infection being treated. Optimal dosages for a given set of conditions can be ascertained by those skilled in the art using conventional dosage determinations or an appropriate adaptation of the experimental data set forth below in Examples 3 and 4.

This invention also relates to a method of treating an active infection in an animal, including humans, wherein said infection is caused by a microorganism which has sterols in its cell membrane, which comprises parenterally administering to such animal a polyene antibiotic emulsion formulation containing a therapeutically effective amount of such antibiotic incorporated into an oil-in-water emulsion. It will be appreciated that the actual preferred amount of a particular polyene antibiotic to be given in each dose during the course of treatment of a particular infection will vary according to the variables discussed above. It will also be appreciated that the optimal course of treatment, i.e., the number of doses of a formulation of this invention given per day for a defined number of days, can be ascertained by those skilled in the art using conventional course of treatment determination tests or an appropriate adaptation of the experimental data set forth below in Example 3 or Example 4. Generally, the total daily dose given during the course of treatment will range from 0.25 mg/kg to 9 mg/kg total body weight.

The active infections which can be effectively treated by the formulations and methods of this invention include all infections caused by microorganisms containing sterols in their cell membranes, such as yeast, other fungi and other eukaryotic organisms, but does not include any prokaryotic organisms since these organisms lack the requisite sterols in their cell membrane. Of particular interest are infections caused by any species of Candida, such as *Candida albicans, Candida tropicalis,* infections caused by *Torulopsis glabrata* and infections caused by any species of *Aspergillus* since these infections are pervasive in immunocompromised patients and/or many people in third world countries.

EXAMPLES

The following Examples illustrate some of the formulations and methods of this invention, and as such, are not to be constructed as limiting.

EXAMPLE 1

Preparation of an Amphotericin B-Intralipid ® 20% Formulation containing a Conventional Concentration of Amphotercin B Amphotericin B (Sigma Chemical Co., St. Louis, Mo.) was incorporated into Intralipid ® 20% oil-in-water emulsion (Cutter Labs. Inc., Berkeley, Calif.) according to the following procedure: Amphotericin B (AMB) was dissolved in dimethylacetamide (DMA) at a concentration of 10–14 mg/ml. The undissolved drug was removed by filtration of this solution through an Acrodisc ®-CR membrane filter (0.45µ, Gelman). The AMB solution in DMA was filtered through a Fluoropore filter (0.2, Millipore) under aseptic conditions. A measured volume of the AMB/DMA solution (0.60 ml) was added to Intralipid ® 20% emulsion (20 ml) in a sterile vial under aseptic conditions to obtain a final drug (AMB)/emulsion (Intralipid ® 20%) concentration of 0.22 mg/ml, and the vial was sealed with a Teflon ® coated rubber stopper. The vial was thoroughly shaken and wrapped with aluminum foil to prevent exposure of the AMB to light. The final emulsion was stored at room temperature.

EXAMPLE 2

Preparation of an Amphotericin B-Intralipid ® 20% Formulation containing a higher than Conventional Concentration of Amphotericin B In order to incorporate concentrations of AMB into Intralipid ® 20% at higher than conventional amounts, the following procedure was employed:

Deoxycholic acid sodium salt (Sigma Chemical Co., St. Louis, Mo.) was dissolved in dimethylacetamide (DMA) at a concentration of 20 mg deoxycholic acid sodium salt (DOCNa) per milliliter of DMA. This solution was used to dissolve amphotericin B (Sigma Chemical Co., St. Louis, Mo.) by mixing the two together and rotating in a 30° C. water bath for 2–4 hours. A concentration of approximately 45 mg/ml of AMB in DOCNa/DMA could be achieved by this method. This AMB solution in DOCNa/DMA was filtered through a Fluoropore ® filter (0.22µ, Millipore) under aspectic conditions. Sometimes, a prefiltration using an Acrodisc ®-CR filter (0.45µ, Gelman) was also required to avoid clogging in the aseptic filtration step. A measured volume of the drug solution (0.30 ml) was added to Intralipid ® 20% emulsion (10 ml) in a sterile vial under aspectic conditions; the final DMA concentration did not exceed 3% of the total volume. The drug solution was added slowly, and the solution and emulsion were mixed by a slow swirling motion of the vial. A final AMB concentration between 1–9 mg/ml was obtained in this way. The vial was closed with a Teflon ® coated rubber stopper and was wrapped with aluminum foil to prevent it from direct exposure to light. The emulsions were stored at room temperature.

EXAMPLE 3

Utility of an Amphotericin B-Intralipid ® 20% Formulation in an Established Candida Albicans Infection in Mice Webster-derived CD-1 male mice (25g) from Charles River Laboratories were injected intravenously (i.v.) with approximately $1.2 \times 10^6$ colony forming units (cfu) of *C. alicans* 3153A in saline for establishment of the infection. C. alibicans 3153A is a strain from Smith Kline & French Laboratories' clinical culture collection. Any strain of C. albicans would be appropriate for use to establish an active infection.

Mice, infected as described above, were injected as described below with either an amphotericin B Intralipid ® 20% formulation prepared according to Example 1, a conventional amphotericin B formulation (Fungizone ®—E. R. Squibb and Son, Princeton, N.J.), or a virulence control formulation consisting of 0.6 ml DMA in 20 ml Intralipid ® 20% prepared according to the procedure of Example 1. Groups of 10 infected mice were used for each drug level or controls. A group of 20 infected mice were used for the virulence control and groups of 10 infected mice were used for the inoculum titration. The preparations of amphotericin B (i.e. emulsion formulated or Fungizone ® formulation) were given as a single injection, i.v., 48 hours after infection. The following dose ranges were used: amphotericin B (Fungizone ®) was administered in two-fold increments from 0.25 mg/kg to 4.0. Amphotericin B in Intralipid ® 20% was administered in two-fold increments from 0.11 to 1.76 mg/kg. Survivors were recorded daily.

The maximum tolerated dose for Fungizone ® injected i.v. was 1.0 mg/kg in the infected mice. Amphotericin B in Intralipid ® 20% was tolerated at 1.76 mg/kg, the highest dose given.

Fifteen days post infection, the time at which all of the virulence controls died, amphtoericin B in Intralipid ® 20% did not appear better in potency than Fungizone ®, i.e., $ED_{50}$ for Fungizone ®=0.25 mg/kg, $ED_{50}$ for amphotericin B in Intralipid ® 20%=0.22 mg/kg. However, the higher levels of amphotericin B tolerated in Intralipid ® 20% did extend survival time beyond that achieved with the highest level of Fungizone ® tolerated.

Furthermore, 1.76 mg/kg of amphotericin B in Intralipid ® 20% increased survival time of 100% of the infected mice so treated to 22 days as compared to a 14 day 100% survival time for infected mice treated with Fungizone ® at 1.0 mg/kg and a 5 day 95% survival time for the virulence controls. Intralipid ® 20% administered to infected mice alone did not increase survival time.

After 31 days, 50% of the mice treated with amphotericin B in Intralipid ® 20%, 1.76 mg/kg, and 10% of the mice treated with Fungizone ®, 1.0 mg/kg, survived the *C. albicans* infection.

EXAMPLE 4

Utility of an Amphotericin B-Intralipid ® 20% Formulation in an Established Candida Albicans Infection in Mice Webster-derived CD-1 male (~25g) from Charles River Laboratories, infected with *C. albicans* as described in Example 3, were given a single infection, i.v., 48 hours after infection with either a virulence control prepared as described in Example 3 (20 mice), the maximum tolerated dose for Fungizone ® (1.0 mg/kg) (10 mice), or amphotericin B in Intralipid ® 20% (9.0 mg/kg) prepared according to the method of Example 2 (10 mice).

The results indicated that all virulence controls were dead by day 14, mice treated with Fungizone ® (1.0 mg/kg) showed 20% survivors at day 34, whereas mice treated with amphotericin B in Intralipid ® 20% (9.0 mg/kg) showed 100% survivors at day 34, the last day of the observation period.

The results stated above in Examples 3 and 4 clearly indicate that administration of conventional dosages of polyene antibiotics, such as amphotericin B formulated in Intralipid ® 20%, result in the same efficacy of the drug as compared to administration of such dosages in conventional formulations, such as amphotericin B formulated in Fungizone ®.

The results stated above in Examples 3 and 4 also clearly indicate that a polyene antibiotic oil-in-water emulsion formulation permits higher than conventional dosages of the polyene antibiotic to be safely, parenterally administered to an animal. Thus, the polyene antibiotic oil-in-water emulsion formulation of this invention effectively increases the therapeutic index of the polyene antibiotic it contains.

Finally, the results stated above in Examples 3 and 4 also clearly indicate that a polyene antibiotic oil-in-water emulsion formulation is efficacious in treating an active infection in an animal, wherein said infection is caused by a microorganism containing sterols in its cell membrane, such as *C. albicans*.

It will be appreciated that the data set out above in Examples 3 and 4 will permit one of skill in the art, upon appropriate modification, to ascertain optimal dosages and courses of treatment depending upon the desired polyene antibiotic to be used, the infection being treated, the host animal involved, the route and site of parenteral administration and other related variables.

EXAMPLE 5

Preparation of a Nystatin-Intralipid ® 20% Emulsion Formulation

A nystatin Intralipid ® 20% emulsion formulation (1.06 mg/ml) was prepared according to the method of Example 1. The nystatin was obtained from Sigma Chemical Co., St. Louis, Mo.

EXAMPLE 6

Evaluation of a Nystatin-Intralipid ® 20% Emulsion Formulation

The nystatin Intralipid ® 20% emulsion formulation prepared in Example 5 was evaluated for pharmacodynamic signs of toxicity. The results indicated that although solubilized nystatin (i.e., conventional formulation) and nystatin Intralipid ® 20% formulation were both tolerated at 8 mg/kg in Webster-derived CD-1 male mice (~25g) from Charles River Laboratories, the experimental animals treated with the emulsion formulation displayed fewer and less severe clinical manifestations of toxicity.

EXAMPLE 7

Preparation of Other Polyene Antibiotic Intralipid ® 20% Emulsion Formulations

Other polyene antibiotics, including, but not limited to, tetraenes other than nystatin, pentaenes such as aliomycin, methylpentatenes such as filipin, carbonylpentaenes such as mycoticin, hexaenes such as cryptocidine, carbonylhexaenes such as dermostatin and heptaenes other than amphotericin B, can be incorporated in Intralipid ® 20% according to the procedure of Example 1 or Example 2.

EXAMPLE 8

Preparation of Other Polyene Antibiotic Oil-in-Water Emulsion Formulations

Oil-in-water emulsions containing sesame seed oil, or greater or less than 20% soybean oil, corn oil, peanut oil, isopropyl myristate or glycerol tripelargonate, or any other non-toxic oil or fat which is capable of parenteral administration, can be employed instead of Intralipid ® 20% according to the procedure of Example 1, Example 2 or Example 7 to prepare the formulation of this invention.

What is claimed is:

1. A package comprising a container of a pharmaceutical formulation suitable for admixture to a parenterally administerable oil-in-water emulsion which formulation includes amphotericin B and dimethylacetamide in an amount sufficient to incorporate the amphotericin B into the oil-in-water emulsion upon admixture, and a second container of an oil-in-water emulsion suitable for parenteral administration.

2. A package of claim 2 wherein the container of the pharmaceutical formulation of amphotericin B and dimethylacetamide includes deoxycholic acid in an amount sufficient to facilitate incorporation of the amphotericin B into the oil-in-water emulsion upon admixture.

3. A package comprising a container of amphotericin B suitable for parenteral administration, a second container of dimethylacetamide suitable for parenteral administration in an amount sufficient to incorporate amphotericin B into an oil-in-water emulsion upon admixture, and a third container of an oil-in-water emulsion suitable for parenteral administration.

4. A package of claim 3 wherein the second container of dimethylacetaide includes deoxycholic acid in an amount sufficient to facilitate incorporation of the amphotericin B into the oil-in-water emulsion.

* * * * *

UNITED STATES PATENT AND TRADEMARK OFFICE
CERTIFICATE OF CORRECTION

PATENT NO.   : 4,831,018
DATED        : May 16, 1989
INVENTOR(S)  : Kirsh, et al.

It is certified that error appears in the above-identified patent and that said Letters Patent is hereby corrected as shown below:

In claim 2 at column 6, line 67, replace "of claim 2" with
-- of claim 1 -- .

Signed and Sealed this

Seventeenth Day of April, 1990

Attest:

HARRY F. MANBECK, JR.

*Attesting Officer*           *Commissioner of Patents and Trademarks*